(12) United States Patent
Konijnenberg

(10) Patent No.: US 11,668,720 B2
(45) Date of Patent: Jun. 6, 2023

(54) METHOD OF PREPARING A BIOLOGICAL SAMPLE FOR STUDY IN A CHARGED PARTICLE DEVICE

(71) Applicant: FEI Company, Hillsboro, OR (US)

(72) Inventor: Albert Konijnenberg, Eindhoven (NL)

(73) Assignee: FEI Company, Hillsboro, OR (US)

( * ) Notice: Subject to any disclaimer, the term of this patent is extended or adjusted under 35 U.S.C. 154(b) by 804 days.

(21) Appl. No.: 16/580,376

(22) Filed: Sep. 24, 2019

(65) Prior Publication Data

US 2020/0132695 A1 Apr. 30, 2020

(30) Foreign Application Priority Data

Oct. 29, 2018 (EP) .................................. 18203184.9

(51) Int. Cl.
| | | |
|---|---|---|
| G01N 33/68 | (2006.01) | |
| G01N 1/28 | (2006.01) | |
| G01N 1/42 | (2006.01) | |
| G01N 33/483 | (2006.01) | |

(52) U.S. Cl.
CPC ....... *G01N 33/6851* (2013.01); *G01N 1/2813* (2013.01); *G01N 1/42* (2013.01); *G01N 33/483* (2013.01)

(58) Field of Classification Search
CPC ............. G01N 33/6851; G01N 33/483; G01N 1/2813; G01N 1/42
See application file for complete search history.

(56) References Cited

U.S. PATENT DOCUMENTS

| | | |
|---|---|---|
| 9,865,428 B2 | 1/2018 | Remigy |
| 2006/0063145 A1 | 3/2006 | Suckau et al. |
| 2007/0278400 A1 | 12/2007 | Schurenberg et al. |
| 2010/0181495 A1 | 7/2010 | Lihl et al. |
| 2016/0245732 A1 | 8/2016 | Rémigy |
| 2017/0350798 A1 | 12/2017 | Carragher et al. |
| 2018/0158661 A1* | 6/2018 | Eberlin ................ G01N 33/487 |

FOREIGN PATENT DOCUMENTS

WO 2018020036 2/2018

* cited by examiner

*Primary Examiner* — Nicole M Ippolito
*Assistant Examiner* — Hanway Chang
(74) *Attorney, Agent, or Firm* — Denton W. McAlister; Thomas F. Cooney

(57) ABSTRACT

The invention relates to a method of preparing a biological sample for study in an analysis device, said method comprising the steps of: providing a biological material to be studied; providing a sample holder that is configured to be placed in said analysis device; and transferring said biological material onto said sample holder for preparing said biological sample. According to the invention, the method comprises the steps of: acquiring a specimen of said biological material provided on said sample holder; transferring said specimen to a screening device for screening said specimen; and evaluating said biological sample based on results obtained by said screening device. With the method, time and resources may be more effectively used in studying biological samples, for example using charged particle microscopy in the form of cryo-EM.

11 Claims, 3 Drawing Sheets

METHOD OF PREPARING A BIOLOGICAL SAMPLE FOR STUDY IN A CHARGED PARTICLE DEVICE

Figure 1:
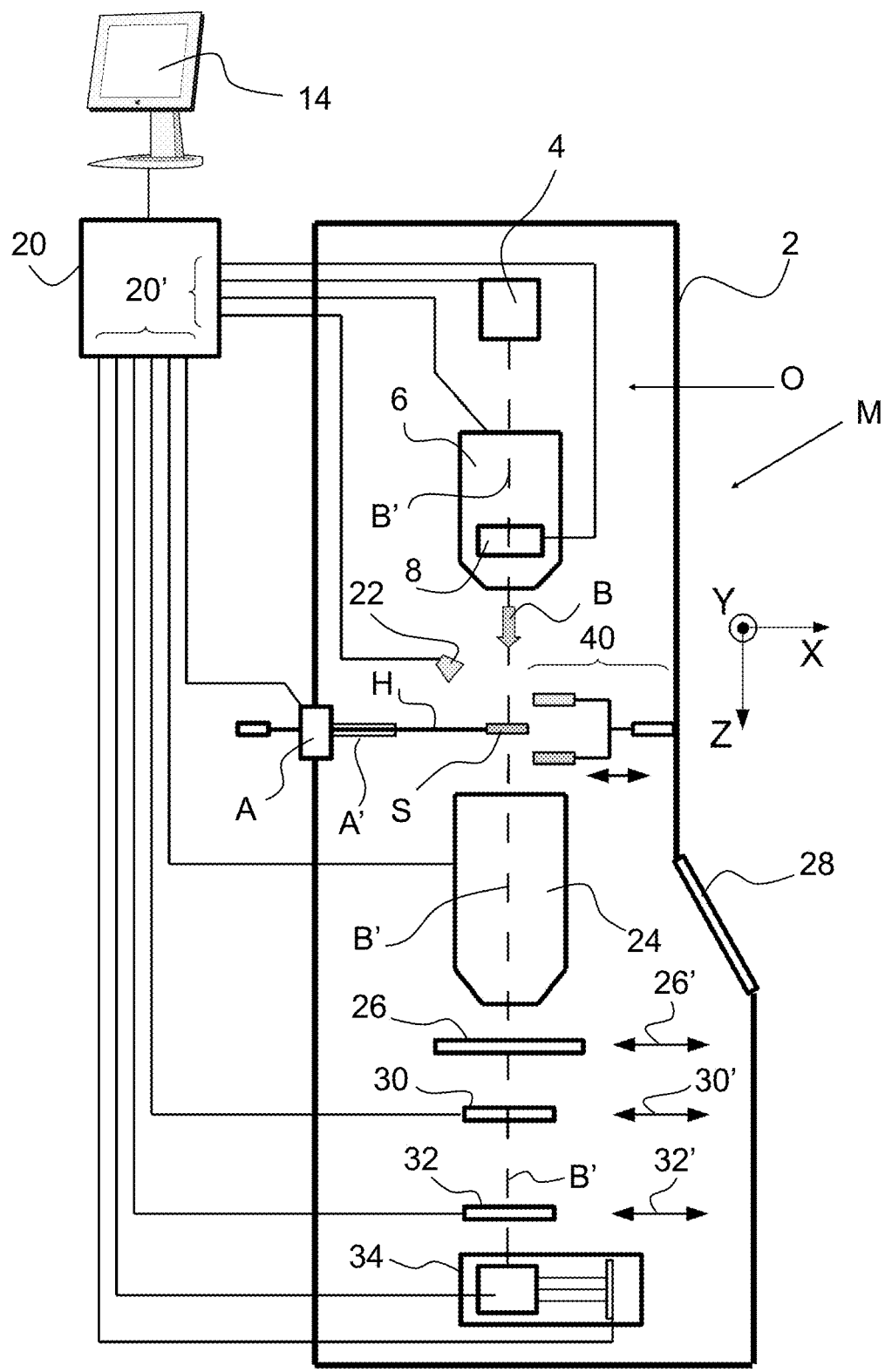

The invention relates to a method of preparing a biological sample for study in a charged particle device.

Biology is the natural science that studies life and living organisms, including their physical structure, chemical processes, molecular interactions, physiological mechanisms, development and evolution.

Cell biology is a branch of biology that studies the structure and function of the cell, the basic unit of life. Cell biology is concerned with the physiological properties, metabolic processes, signalling pathways, life cycle, chemical composition and interactions of the cell with their environment. In cell biology, molecular recognition between macromolecules governs all of the most sophisticated processes in cells. The most common macromolecules comprise biopolymers (nucleic acids, proteins, carbohydrates and lipids) and large non-polymeric molecules (such as lipids and macrocycles).

Many researchers are interested in studying macromolecular complexes in their natural environment at high resolution in order to reveal their structural dynamics and interactions. To this end, charged particle microscopy may be used. Charged particle microscopy is a well-known and increasingly important technique for imaging microscopic objects, particularly in the form of electron microscopy (EM). Historically, the basic genus of electron microscope has undergone evolution into a number of well-known apparatus species, such as the Transmission Electron Microscope (TEM), Scanning Electron Microscope (SEM), and Scanning Transmission Electron Microscope (STEM), and also into various sub-species, such as so-called "dual-beam" tools (e.g. a FIB-SEM), which additionally employ a "machining" Focused Ion Beam (FIB), allowing supportive activities such as ion-beam milling or Ion-Beam-Induced Deposition (IBID), for example.

EM provides a number of ways to study biological samples: conventional TEM is used to study gross morphology of biological samples; electron crystallography and single-particle analysis are dedicated to study proteins and macromolecular complexes; and (cryo-)electron tomography and Cryo-EM of vitreous sections (CEMOVIS) are aimed at cellular organelles and molecular architectures. In Cryo-EM and CEMOVIS, samples are preserved by rapid freezing using a vitrification technique, and observed by cryo-TEM. CEMOVIS additionally includes the cryo-sectioning of the sample, which may be done using a cryo-FIB technique.

Preparing a biological sample for study in an analysis device often is time consuming and labour intensive. One of the drawbacks associated with these studies is that only after the biological sample is prepared and studied in the analysis device, the user knows whether the preparation of the biological sample was successful or not.

Preparing a Cryo-EM specimen, for example, comprises the steps of taking an aqueous sample of a biological material (usually a purified protein complex), applying it to a support structure (grid), reducing its dimension to a layer that is as thin as possible (~100-800 Å depending on the size of the biological molecule), and then freezing this layer fast enough to prevent the water from crystallising. Many aspects of this process of preparing a biological sample are problematic.

One of the challenges lies in acquiring a thin layer of the sample on the support structure.

In US 2010/181495 A1, a method and a device for preparing specimens for a cryo-electron microscope are described. Here, a carrier is fixed to a holder, sample liquid is applied to the carrier, and a blotting device for removing excess sample liquid from the carrier by means of the absorbing medium is applied. The absorbing medium is illuminated with light and a change in the optical properties of the absorbing medium is detected by means of an optical sensor device. A control moves the blotting away from the carrier depending on a change in the detected optical properties. This improves the reproducibility of the step of obtaining a thin layer.

Since the blotting step is difficult to establish in a reproducible way, US 2017/350798 A1 proposes a method and a device where the requirement for blotting of excess fluid may be minimized or eliminated by reducing the volume of the sample from microliter scale to picoliter scale.

Even though the blotting step provides a challenge, many other aspects of the above process of preparing a biological sample are challenging and unpredictable as well. The purified complex may encounter microscopic surfaces, materials and dynamics that change said purified complex. Often, these changes are only visible once the sample on the grid has been examined in the Cryo-EM. Thus, valuable resources, including scientist preparation time and expensive EM use time, may be wasted to no avail.

In view of this, it is an object of the present disclosure to provide techniques for improved preparation of a biological sample for study in a charged particle device, and in particular techniques that prevent the waste of valuable resources as described above.

To this end, the present disclosure provides techniques for preparing a biological sample for study in an analysis device as defined in claim 1. Said analysis device as defined herein is a charged particle device, such as a charged particle microscope in the form of an electron microscope. It is noted however, that said analysis device may in general be any analysis device that requires a lot of resources, in particular time and money, to analyse the biological sample.

In particular, the analysis device may be an EM apparatus, such as a cryo-TEM. These are relatively expensive and require a lot of time for analyzing a sample. Other microscopes, such as optical, fluorescence, and scanning probe microscopes, are relatively costly as well. The same holds true for an x-ray diffractometer, for example.

The techniques according to the present disclosure comprise the step of providing a biological material to be studied in said analysis device. Said biological material can be cells, cell components, single-cellular organisms, macromolecules such as protein complexes, and the like. It is conceivable that said biological material needs to be stored and studied in a body of aqueous liquid. Said liquid may be water, electrolyte, cell fluid, blood plasma, and the like. The aqueous liquid may also comprise one or more buffer solutions.

The disclosed techniques further comprise the step of providing a sample holder that is configured to be placed in the analysis device. The sample holder may, in some embodiments, be any suitable container that can be used in the analysis device. In other embodiments, the sample holder is specifically configured to be placed in the analysis device, for example due to the fact that the sample holder is configured to mate with a specific recess in said analysis device. In a specific embodiment, the sample holder is an EM grid.

Once the biological material and the sample holder are provided, said biological material is transferred onto said sample holder for preparing said biological sample. It is conceivable that, after transferring, the sample holder is fully ready to be studied in the analysis device. Alternatively, it may be required that one or more additional steps, such as a vitrification step in case of cryo-EM, are necessary to compete the preparation of the biological sample. Thus in an embodiment the techniques may further comprise the step of subjecting said biological material on said sample holder to rapid cooling using a cryogen for preparing said biological sample.

To contribute to using resources in an effective way, the techniques as disclosed herein provide the additional steps of acquiring a specimen of said biological material and screening said specimen in a screening device. Then, the results of said screening may be used to evaluate said biological sample. Said evaluating may comprise the step of defining a quality grade of said biological sample. For example, based on the results obtained by said screening device, it may be decided that the biological sample is not sufficiently prepared to be studied in the analysis device. Thus, it may be decided to not pursue the study in the analysis device, saving precious resources.

Thus, a part of the sample that is already provided on the sample holder is taken as a specimen, and then this specimen is screened in turn. In doing so, many possible interactions between the sample and the environment during sample preparation are already accounted for, enabling a reliable and representative outcome of the screening. In particular, the specimen may be screened before the actual sample is studied in the analysis device, and thus evaluation of the result may include deciding that this particular biological sample is, or is not, to be studied in the analysis device. In that case, the techniques as described above ensures that resources are effectively used. With this, the object of the disclosure is achieved.

The techniques may comprise, in an embodiment, the step of transferring said sample holder with said biological sample into said analysis device, and analyzing said biological sample. This step may be conditionally performed, for example based on the evaluation of the results of the screening device. In an embodiment, said step of transferring and analyzing said biological sample is performed only when a certain minimum quality grade is defined for said biological sample.

Alternatively, or additionally, said step of evaluating is used to enhance the information obtained in analyzing said biological sample. The screening may thus be used to interpret the results of the study of the biological sample in the analysis device. The evaluation of the biological specimen may thus be used to increase the intelligibility of the study of the biological sample. For example the screening might reveal the oligomeric compositions of the analyte or provide evidence for post translational modifications, which would otherwise go unnoticed in the sample analysis.

According to the disclosure, a technique is provided for preparing a biological sample for study in a charged particle device, said technique comprising the steps of:
  providing a biological material to be studied;
  providing a sample holder that is configured to be placed in said charged particle device;
  transferring said biological material onto said sample holder for preparing said biological sample; and
  acquiring a specimen of said biological material provided on said sample holder, and performing ambient ionization mass spectrometry on said specimen.

The technique may comprise the step of preparing a biological sample, in particular a protein complex, for study in a charged particle device, in particular an electron microscope, such as a Cryo-EM. Said biological sample may be provided on a suitable support structure, such as an EM grid. Then, once the biological sample is provided on the support structure, a part of that sample is taken as a specimen, and ambient ionization mass spectrometry is performed for orthogonal analysis (i.e. screening) on said specimen. Thus, in effect, the screening device as defined herein comprises a mass spectrometer.

Sample screening by native mass spectrometry yields relevant information on one or more aspects of the biological sample, and in particular of protein complexes. These aspects include, for example, sample purity, integrity and homogeneity of the biological sample; protein complex stoichiometry; protein identity and sequence information; post translational modifications; small molecule binding. Based on this information, it is possible to evaluate whether the prepared sample can be successfully studied using charged particle microscopy. For example, structural information obtained with mass spectrometry can be reported directly to the user for eliminating unpromising samples. Information can either be obtained through a protein-centric method, wherein the sample carrier is not further treated prior to analysis and (structural) information is obtained from intact biomolecules, or through a peptide-centric method, wherein the sample carrier is treated prior to analysis for what is known to artisans as a bottom-up proteomics approach. Thus, screening of the biological specimen using mass spectrometry may be used to enhance, or interpret, the results obtained by the charged particle microscopy.

The ambient ionization mass spectrometry may comprise one or more techniques chosen from the group consisting of: paperspray ionization; liquid extraction surface analysis; desorption electrospray ionization. Other techniques are conceivable as well.

From the above it follows that combining biological sample preparation for study in charged particle microscopy, with mass spectrometry, may provide a full workflow for rapid screening of samples on grids before cryo-electron microscopy.

In an embodiment, the technique comprises the step of providing said biological material to be studied in a solution. For example, the biological material to be studied may be provided, and the technique may comprise the step of preparing a solution with said biological material. The solution, such as a protein complex provided in an aqueous liquid comprising one or more buffers, may then be transferred onto said sample holder.

In an embodiment, said step of acquiring a specimen of said biological material transferred onto said sample holder comprises the step of acquiring said specimen using an absorption technique. Such a technique is suitable for easy, reliable and rapid acquisition of biological material that is provided on a sample holder. It is noted in this regard that the absorption technique as defined herein includes both absorption phenomena, i.e. where accumulation takes place in the bulk of a carrier, as well as adsorption phenomena, i.e. where accumulation takes place at a surface of a carrier.

As an example, it is noted that in particular for preparing a Cryo-EM specimen, it is important that the layer provided on the sample holder is as thin as possible. To this end, once the aqueous sample of biological material is applied to the support structure (grid), a blotting paper is normally used to ensure that superfluous sample is removed and the biological sample layer is as thin as possible. This general technique of absorption may advantageously be used to acquire the biological specimen for use in the screening device.

In an embodiment, said blotting as an absorption technique may advantageously be used in the techniques as described herein, in particular when a blotting material such as blotting paper is used, in that said blotting material is at least partly used in said step of performing ambient ionization mass spectrometry. It was found that ambient ionization mass spectrometry is particularly useful for biological samples. Additionally, the sample concentrations required for performing EM and MS are roughly the same. In this embodiment, the blotting material that is already used in EM sample preparation (and normally discarded of) is advantageously used in a screening method to evaluate whether the EM sample can be studied in the EM. Here, the specimen that is present in (or on) the blotting material has a high degree of similarity to the sample that is present on the EM grid, leading to reliable and predictable results of the screening device. Additionally, it is envisaged that this embodiment of the technique may be easily automated as well, such that controlled sample preparation and screening is possible.

Manipulation of the blotting material, such as blotting paper, is conceivable. For example, it is conceivable that a part of the blotting material is removed or cut before performing said step of ambient ionization mass spectrometry. In an embodiment, the blotting material is used multiple times, each time for different samples, and the blotting material is cut into corresponding pieces to test each individual sample using ambient ionization mass spectrometry. This is useful in automating sample preparation.

Figure 2:
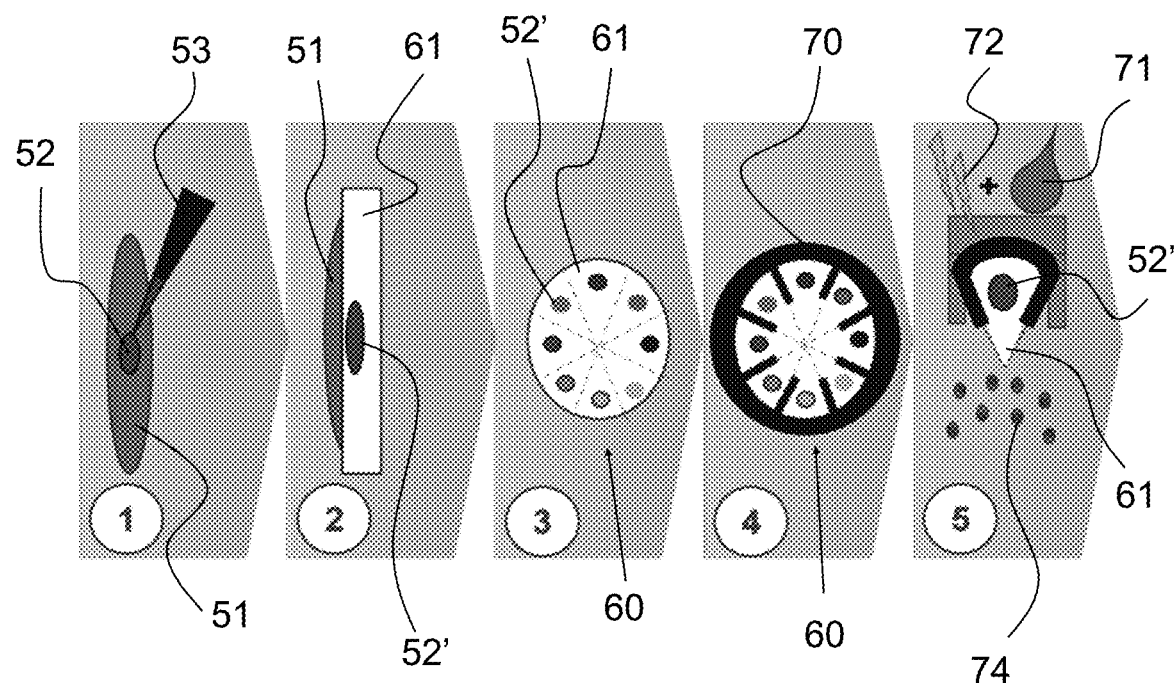
Figure 3:
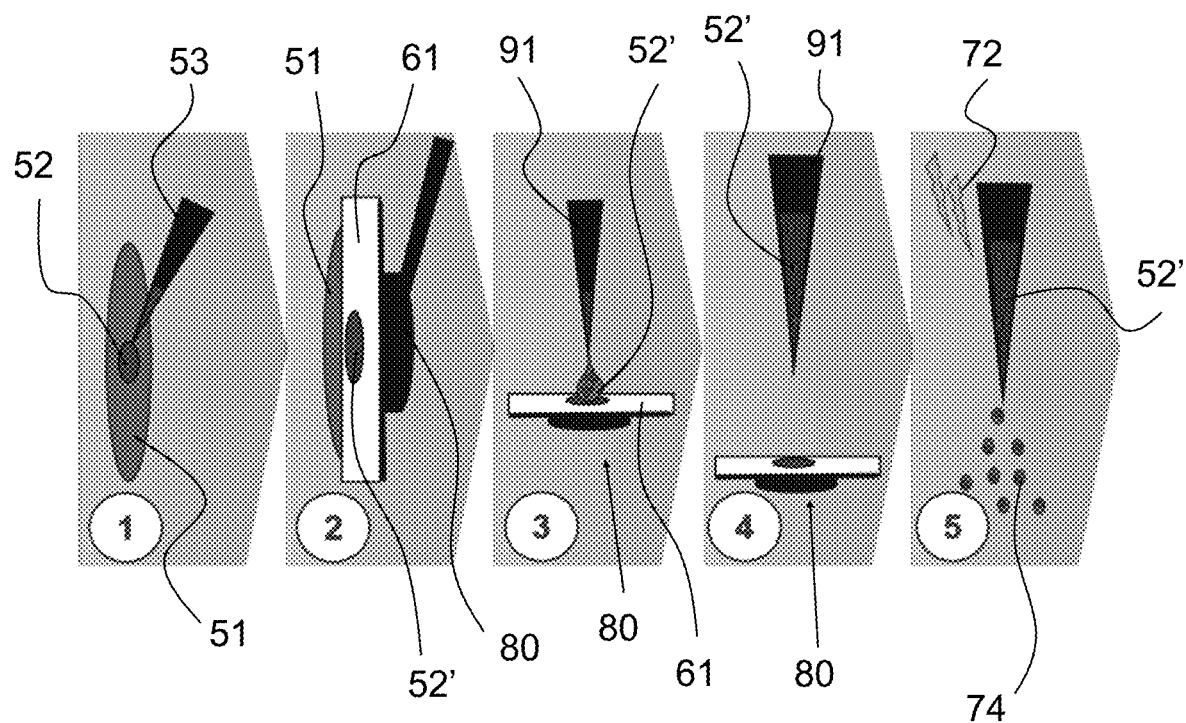
Figure 4:
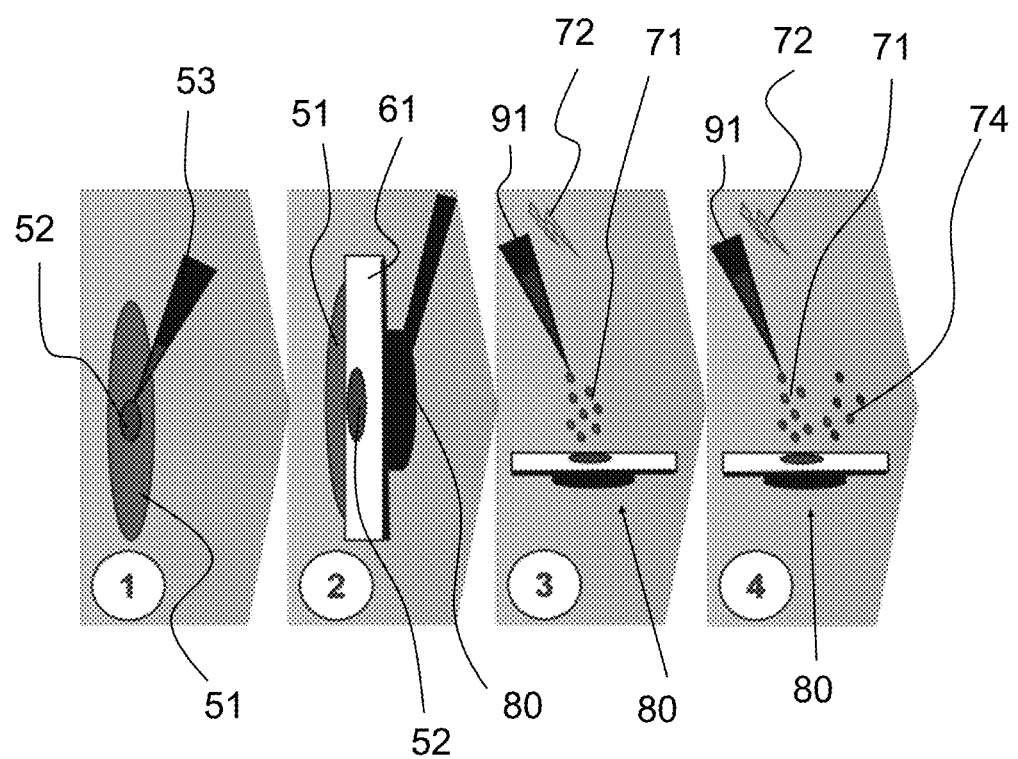

The invention will now be elucidated in more detail on the basis of exemplary embodiments and the accompanying schematic drawings, in which:

FIG. 1—shows a longitudinal cross-sectional view of a charged particle microscope according to a first embodiment of the invention;

FIG. 2—shows a first embodiment of a method for screening a biological sample that is being prepared as a sample for study in a charged particle microscope;

FIG. 3—shows a second embodiment of a method for screening a biological sample that is being prepared as a sample for study in a charged particle microscope;

FIG. 4—shows a third embodiment of a method for screening a biological sample that is being prepared as a sample for study in a charged particle microscope;

FIG. 1 (not to scale) is a highly schematic depiction of an embodiment of a charged-particle microscope M that can be used as analysis device in an embodiment of the method according to the invention. More specifically, it shows an embodiment of a transmission-type microscope M, which, in this case, is a TEM/STEM (though, in the context of the current invention, it could just as validly be a SEM (see FIG. 2), or an ion-based microscope, for example). In FIG. 1, within a vacuum enclosure 2, an electron source 4 produces a beam B of electrons that propagates along an electron-optical axis B' and traverses an electron-optical illuminator 6, serving to direct/focus the electrons onto a chosen part of a biological sample S (which may, for example, be (locally) thinned/planarized). Also depicted is a deflector 8, which (inter alia) can be used to effect scanning motion of the beam B.

The biological sample S is held on a sample holder H, in this case a supporting structure in the form of a grid (not shown), and this sample holder H can be positioned in multiple degrees of freedom by a positioning device/stage A, which moves a cradle A' into which holder H is (removably) affixed; for example, the specimen holder H may comprise a finger that can be moved (inter alia) in the XY plane (see the depicted Cartesian coordinate system; typically, motion parallel to Z and tilt about X/Y will also be possible). Such movement allows different parts of the sample S to be illuminated/imaged/inspected by the electron beam B traveling along axis B' (in the Z direction) (and/or allows scanning motion to be performed, as an alternative to beam scanning). If desired, a cooling device (not depicted, but known to those skilled in the art) can be brought into intimate thermal contact with the sample holder H, so as to maintain it (and the sample S thereupon) at cryogenic temperatures, for example.

The electron beam B will interact with the sample S in such a manner as to cause various types of "stimulated" radiation to emanate from the sample S, including (for example) secondary electrons, backscattered electrons, X-rays and optical radiation (cathodoluminescence). If desired, one or more of these radiation types can be detected with the aid of detector device 22, which might be a combined scintillator/photomultiplier or EDX (Energy-Dispersive X-Ray Spectroscopy) module, for instance; in such a case, an image could be constructed using basically the same principle as in a SEM. However, alternatively or supplementally, one can study electrons that traverse (pass through) the sample S, exit/emanate from it and continue to propagate (substantially, though generally with some deflection/scattering) along axis B'. Such a transmitted electron flux enters an imaging system (projection lens) 24, which will generally comprise a variety of electrostatic/magnetic lenses, deflectors, correctors (such as stigmators), etc. In normal (non-scanning) TEM mode, this imaging system 24 can focus the transmitted electron flux onto a fluorescent screen 26, which, if desired, can be retracted/withdrawn (as schematically indicated by arrows 26') so as to get it out of the way of axis B'. An image (or diffractogram) of (part of) the sample S will be formed by imaging system 24 on screen 26, and this may be viewed through viewing port 28 located in a suitable part of a wall of enclosure 2. The retraction mechanism for screen 26 may, for example, be mechanical and/or electrical in nature, and is not depicted here.

As an alternative to viewing an image on screen 26, one can instead make use of the fact that the depth of focus of the electron flux leaving imaging system 24 is generally quite large (e.g. of the order of 1 meter). Consequently, various other types of analysis apparatus can be used downstream of screen 26, such as:

TEM camera 30. At camera 30, the electron flux can form a static image (or diffractogram) that can be processed by controller/processor 20 and displayed on a display device (not depicted), such as a flat panel display, for example. When not required, camera 30 can be retracted/withdrawn (as schematically indicated by arrows 30') so as to get it out of the way of axis B'.

STEM camera 32. An output from camera 32 can be recorded as a function of (X,Y) scanning position of the beam B on the sample S, and an image can be constructed that is a "map" of output from camera 32 as a function of X,Y. Camera 32 can comprise a single pixel with a diameter of e.g. 20 mm, as opposed to the matrix of pixels characteristically present in camera 30. Moreover, camera 32 will generally have a much higher acquisition rate (e.g. $10^6$ points per second) than camera 30 (e.g. $10^2$ images per second). Once again, when not required, camera 32 can be retracted/withdrawn (as schematically indicated by arrows 32') so as to get it out of the way of axis B' (although such retraction would not be a necessity in the case of a donut-shaped annular dark field camera 32, for example; in such a camera, a central hole would allow flux passage when the camera was not in use).

As an alternative to imaging using cameras 30 or 32, one can also invoke spectroscopic apparatus 34, which could be an EELS module, for example.

It should be noted that the order/location of items 30, 32 and 34 is not strict, and many possible variations are conceivable. For example, spectroscopic apparatus 34 can also be integrated into the imaging system 24.

In the embodiment shown, the microscope M further comprises a retractable X-ray Computed Tomography (CT) module, generally indicated by reference 40. In Computed Tomography (also referred to as tomographic imaging) the source and (diametrically opposed) detector are used to look through the specimen along different lines of sight, so as to acquire penetrative observations of the sample from a variety of perspectives.

Note that the controller (computer processor) 20 is connected to various illustrated components via control lines (buses) 20'. This controller 20 can provide a variety of functions, such as synchronizing actions, providing setpoints, processing signals, performing calculations, and displaying messages/information on a display device (not depicted). Needless to say, the (schematically depicted) controller 20 may be (partially) inside or outside the enclosure 2, and may have a unitary or composite structure, as desired.

The skilled artisan will understand that the interior of the enclosure 2 does not have to be kept at a strict vacuum; for example, in a so-called "Environmental TEM/STEM", a background atmosphere of a given gas is deliberately introduced/maintained within the enclosure 2. The skilled artisan will also understand that, in practice, it may be advantageous to confine the volume of enclosure 2 so that, where possible, it essentially hugs the axis B', taking the form of a small tube (e.g. of the order of 1 cm in diameter) through which the employed electron beam passes, but widening out to accommodate structures such as the source 4, specimen holder H, screen 26, camera 30, camera 32, spectroscopic apparatus 34, etc.

Now referring to FIGS. 2 to 4, different embodiments of preparing a biological sample for study in an analysis device, for example the charged particle microscope depicted in FIG. 1, are shown.

Generally, the method shown in these FIGS. 2 to 4 comprises the sub-steps of:
(1) providing an aqueous sample of a biological material 52, such as a purified protein complex, and applying it to a sample holder 51 (here a support structure such as an EM grid);
(2) obtaining a biological specimen 52' of said sample already provided on said sample holder 51, in the embodiments shown by means of an absorption technique using an absorption material 61, such as a blotting paper 60, 61; and
(3)-(5) processing said biological specimen 52' (in FIGS. 3 and 4), preparing said biological specimen 52' for screening in a screening device. In the embodiments shown, different kinds of ambient ionization mass spectrometry are used for screening said biological specimen. These kinds of ambient ionization mass spectrometry techniques are described in more detail below.

FIG. 2 shows so called paperspray ionization of blotting paper. In step 1, a biological sample 52 is provided on a sample holder 51 by means of a supply nozzle 53. In step 2, the blotting paper 61 is used to remove excess sample 52 and to reduce the dimension of the sample 52 to a layer that is as thin as possible in order to be able to vitrify the sample in a subsequent step (not shown). Details of the process for vitrifying these samples can be obtained, for example, from U.S. Pat. No. 9,865,428 B2; and these processes are known per se to those skilled in the art. This blotting as shown in step 2 may be done for a plurality of identical, or different, samples. As shown in step 3, the blotting paper 60 may contain a plurality of pie pieces 61, which may now thus comprise a plurality of the same, or different, screening specimens 52' that are representative for the corresponding samples 52 on the sample holder 51. The blotting material 60 is then transferred to holder 70 that punctures triangles out of the blotting paper to separate the various blotted screening samples 52'. These triangles 61 are then transferred to a stage of a mass spectrometer. In order to extract and ionize the sample for analysis by mass spectrometry, a compatible extraction buffer 71 is aspirated on the blotting paper 61 and a high voltage (1-5 kV) is applied to generate a jet of small droplets 74 into the source of the mass spectrometer for analysis.

In FIG. 3, liquid extraction electrospray ionization of blotting material is used as a screening aid. The process is similar to the process of FIG. 2, but here use is made of a blotting device 80 for acquiring a specimen 52' on the blotting material 61. The blotting device 80 may then be transferred in its entirety to a liquid extraction surface analysis (LESA) stage holder. Here, as shown in step 3, a pipette 91 filled with a mass spectrometry compatible buffer is applying a droplet to the surface of the blotting material 61 that contains the biological specimen 52'. The droplet is held there for a few seconds, allowing diffusion of the analyte molecules from the surface to take place through forming of a liquid micro-junction. The pipette 91 now contains a part of the specimen 52' (step 4) and can be brought to the source of the mass spectrometer (step 5), where a voltage 72 is applied to generate a jet of small droplets 74 into the source of the mass spectrometer for analysis. It is also possible to reaspirate the solution and introduce it to the mass spectrometer via conventional (nano)ESI using an emitter.

FIG. 4 shows desorption electrospray ionization of blotting material. The process is similar as described with respect to FIGS. 2 and 3. Here, like in FIG. 3, use is made of the blotting device 80, which is transferred to act as a desorption ESI stage holder. Here, a conductive emitter 91 is filled with a mass spectrometry compatible buffer 71 to which a voltage 72 is applied, generating a stream of charged droplets 71 wetting the blotting material. Upon interaction with the blotted specimen 52', some droplets are ejected as charge droplets 74 again, containing the analyte. These droplets 74 can then be introduced into the vacuum of the mass spectrometer for analysis.

Above, the invention has been explained by means of several examples. The invention is not limited to the examples described above.

In general, the method as described herein is in particular advantageous when preparing a biological sample for analysis in an analysis device takes a lot of resources, for example due to the fact that: the actual preparation takes a lot of time; the process of successfully preparing said biological sample are uncertain; and/or the cost per time unit of the analysis device are relatively high. This is in particular true for study of a biological sample in a charged particle device. In these cases, taking a specimen of the biological sample, and using a orthogonal screening device for assessing and evaluating whether the biological sample can be successfully analysed in the analysis device, provides at least an increased confidence in the process of analyzing a biological sample.

The method as described herein is in particular suitable for use in EM sample preparation. In EM sample preparation, current limitations include: sample loss; low throughput; and sample consumption. With the method as described herein, at least one or more of these limitations are addressed. Currently, preparations of grids for Cyro-EM lead to a 99.9% loss of proteins that get absorbed to the blotting material, such as blotting paper. This blotting paper currently serves no purpose, and is disposed. According to an embodiment of the method as described herein, the blotting material is advantageously used for screening the biological sample on the grid, using in particular mass spectrometry. This technique is relatively cheap and fast (in the order of seconds to minutes per paper sample), thus giving valuable information at an early stage in the study of the biological sample. Additionally, it can be used for high throughput screening of even large sample of sets. This way, it is possible to select the right buffer solutions, for example, or other conditions, that are needed to successfully prepare a biological sample for study in the electron microscope.

Furthermore, by screening the biology prior to taking the samples to the electron microscope, the user will gain a higher throughput by omitting unnecessarily time-, resources- and sample consuming pre-screening steps in the electron microscope through e.g. negative staining EM, limiting high throughput analysis.

The desired protection is defined by the appended claims.

The invention claimed is:

1. A method of preparing a biological sample for study in a charged particle microscope device, said method comprising:
   providing a biological material;
   providing a sample holder that is configured to be placed in said charged particle microscope device;
   transferring said biological material onto said sample holder for preparing said biological sample;
   acquiring a specimen of said biological material provided on said sample holder, wherein said acquiring comprises acquiring said specimen using an absorption technique that comprises blotting using a blotting paper; and
   performing ambient ionization mass spectrometry on said specimen.

2. The method of claim 1, wherein said blotting paper is at least partly used in performing ambient ionization mass spectrometry.

3. The method of claim 1, comprising evaluating said biological sample based on results obtained by said ambient ionization mass spectrometry.

4. The method of claim 3, wherein said evaluating comprises defining a quality grade of said biological sample.

5. The method of claim 1, comprising transferring said sample holder with said biological sample into said charged particle microscope device, and analyzing said biological sample using said charged particle microscope device.

6. The method of claim 5, wherein transferring and analyzing said biological sample using said charged particle microscope device is performed only when a certain minimum quality grade is defined for said biological sample.

7. The method of claim 6, further comprising evaluating said biological sample based on results obtained by said ambient ionization mass spectrometry wherein said evaluating is used to enhance the information obtained in analyzing said biological sample.

8. The method of claim 1, wherein said ambient ionization mass spectrometry comprises one or more techniques chosen from the group consisting of: paperspray ionization, liquid extraction surface analysis, and desorption electrospray ionization.

9. The method of claim 1, wherein said sample holder comprises a grid.

10. The method of claim 1, further comprising subjecting said biological material on said sample holder to rapid cooling using a cryogen for preparing said biological sample.

11. The method of claim 1, wherein said biological material to be studied is supplied in a solution, and said solution is transferred onto said sample holder.

* * * * *